(12) United States Patent
Morimoto

(10) Patent No.: US 10,456,109 B2
(45) Date of Patent: Oct. 29, 2019

(54) ULTRASONIC ENDOSCOPE

(71) Applicant: FUJIFILM Corporation, Tokyo (JP)

(72) Inventor: Yasuhiko Morimoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 321 days.

(21) Appl. No.: 15/280,257

(22) Filed: Sep. 29, 2016

(65) Prior Publication Data
US 2017/0014099 A1 Jan. 19, 2017

Related U.S. Application Data

(63) Continuation of application No. PCT/JP2015/059184, filed on Mar. 25, 2015.

(30) Foreign Application Priority Data

Mar. 31, 2014 (JP) .................................. 2014-071316

(51) Int. Cl.
A61B 8/00 (2006.01)
A61B 8/12 (2006.01)
(Continued)

(52) U.S. Cl.
CPC ............ *A61B 8/445* (2013.01); *A61B 1/0008* (2013.01); *A61B 1/00082* (2013.01); *A61B 8/12* (2013.01);
(Continued)

(58) Field of Classification Search
CPC ..... A61B 8/445; A61B 8/4416; A61B 8/5207; A61B 8/461; A61B 1/00082; A61B 1/0008; A61B 8/12
See application file for complete search history.

(56) References Cited

U.S. PATENT DOCUMENTS 5,614,660 A * 3/1997 Tanaka ............... A61B 1/00142
600/115
5,766,151 A * 6/1998 Valley .............. A61B 17/00234
604/103.07
(Continued)

FOREIGN PATENT DOCUMENTS

JP 62-186701 U 11/1987
JP 5-305086 A 11/1993
(Continued)

OTHER PUBLICATIONS

Chinese Office Action and Search Report, dated Jun. 27, 2018 for corresponding Chinese Application No. 201580016733.7, with English translations.
(Continued)

*Primary Examiner* — Sanjay Cattungal
(74) *Attorney, Agent, or Firm* — Birch, Stewart, Kolasch & Birch, LLP

(57) ABSTRACT

The ultrasonic endoscope includes: an insertion part that includes a tip, a base end, and a longitudinal axis; an ultrasonic transducer that is provided at the tip of the insertion part; a locking groove that is a balloon mounting portion which is disposed closer to the base end of the insertion part than the ultrasonic transducer is and on which a balloon wrapping the ultrasonic transducer is detachably mounted; a balloon pipe line that extends in the insertion part; a tip-side opening surface of the balloon pipe line that is provided closer to the tip than the locking groove and has components normal to a direction of the longitudinal axis; and a groove portion which is formed toward the tip from the tip-side opening surface as a starting point and of which at least a part overlaps the ultrasonic transducer in the direction of the longitudinal axis.

7 Claims, 10 Drawing Sheets

(51) Int. Cl.
*A61B 1/00* (2006.01)
*A61B 8/08* (2006.01)

(52) U.S. Cl.
CPC ............ *A61B 8/4416* (2013.01); *A61B 8/461* (2013.01); *A61B 8/5207* (2013.01)

(56) References Cited

U.S. PATENT DOCUMENTS

| | | | | |
|---|---|---|---|---|
| 5,879,499 | A * | 3/1999 | Corvi | A61M 25/0012 156/173 |
| 5,967,984 | A * | 10/1999 | Chu | A61B 8/12 600/439 |
| 6,142,945 | A * | 11/2000 | Sakamoto | A61B 1/018 600/459 |
| 6,547,788 | B1 * | 4/2003 | Maguire | A61B 18/00 606/41 |
| 2003/0045768 | A1 * | 3/2003 | Hirooka | A61B 8/0841 600/2 |
| 2006/0195016 | A1 * | 8/2006 | Fujikura | A61B 1/00082 600/116 |
| 2007/0249940 | A1 * | 10/2007 | Kohno | A61B 1/00082 600/463 |
| 2009/0099414 | A1 * | 4/2009 | Goto | A61B 1/267 600/106 |
| 2010/0331883 | A1 * | 12/2010 | Schmitz | A61B 10/0275 606/249 |
| 2014/0018788 | A1 * | 1/2014 | Engelman | A61B 18/18 606/33 |
| 2014/0350401 | A1 * | 11/2014 | Sinelnikov | A61B 8/54 600/439 |
| 2016/0016016 | A1 * | 1/2016 | Taylor | A61N 7/022 606/169 |

FOREIGN PATENT DOCUMENTS

| | | |
|---|---|---|
| JP | 2003-116857 A | 4/2003 |
| JP | 2006-230950 A | 9/2006 |
| JP | 2009-207758 A | 9/2009 |
| JP | 2009-240657 A | 10/2009 |
| WO | WO 2011/108157 A1 | 9/2011 |
| WO | WO 2014/010283 A1 | 1/2014 |

OTHER PUBLICATIONS

International Preliminary Report on Patentability for PCT/JP2015/059184 (PCT/IPEA/409) completed on Apr. 12, 2016.
International Search Report for PCT/JP2015/059184 (PCT/ISA/210) dated Jun. 30, 2015.
Written Opinion of the International Searching Authority for PCT/JP2015/059184 (PCT/ISA/237) dated Jun. 30, 2015.
Extended European Search Report, dated Feb. 20, 2017, for counterpart European Application No. 15772585.4.
Chinese Office Action and Search Report, dated Feb. 11, 2019 for counterpart Chinese Application No. 201580016733.7, with English translation.
Chinese Office Action and Search Report dated Jul. 8, 2019, for counterpart Chinese Patent Application No. 201580016733.7, with English translation.

* cited by examiner

ULTRASONIC ENDOSCOPE

CROSS-REFERENCE TO RELATED APPLICATIONS

This application is a Continuation of PCT International Application No. PCT/JP2015/059184 filed on Mar. 25, 2015, which claims priority under 35 U.S.C. § 119(a) to Japanese Patent Application No. 2014-071316 filed on Mar. 31, 2014. Each of the above applications is hereby expressly incorporated by reference, in their entirety, into the present application.

BACKGROUND OF THE INVENTION

1. Field of the Invention

The present invention relates to an ultrasonic endoscope, and more particularly, to an ultrasonic endoscope where a balloon can be mounted on a tip portion of an insertion part to be inserted into a body cavity.

2. Description of the Related Art

In the related art, an ultrasonic endoscope has been used in a medical field. The ultrasonic endoscope includes an imaging element and a plurality of ultrasonic transducers that are integrally disposed at a tip portion of an insertion part to be inserted into a body cavity of a subject. Each of the ultrasonic transducers generates ultrasonic waves toward a portion to be observed in the body cavity and receives ultrasonic echoes (echo signals) reflected by the portion to be observed, and electrical signals (ultrasonic wave-detection signals) corresponding to the received ultrasonic echoes are output to an ultrasonic observation device (ultrasonic processor device). Then, after various kinds of signal processing are performed in the ultrasonic observation device, the electrical signals are displayed on a monitor or the like as an ultrasonic tomographic image.

Since the ultrasonic waves and the echo signals are significantly attenuated in the air, an ultrasonic transmission medium (for example, water, oil, or the like) needs to be interposed between the ultrasonic transducers and the portion to be observed. Thus, a stretchable bag-shaped balloon is mounted on a tip portion of the ultrasonic endoscope, and an ultrasonic transmission medium is injected into the balloon so that the balloon is inflated and is in contact with the portion to be observed. Accordingly, air is excluded from a space between the ultrasonic transducers and the portion to be observed, so that the attenuation of the ultrasonic waves and the echo signals is prevented.

A supply/discharge pipe line (supply/discharge pipe line for a balloon) is inserted into the insertion part of the ultrasonic endoscope in order to supply and discharge an ultrasonic transmission medium into and from the balloon. The supply/discharge pipe line includes a supply/discharge port (tip opening) opening to the tip portion of the insertion part, and an ultrasonic transmission medium is supplied into and discharged from the balloon through the supply/discharge port.

Further, the ultrasonic endoscope is cleaned and sterilized after endoscopy, and the supply/discharge pipe line needs to be brushed. Particularly, since liquid, residue, and the like are likely to enter the supply/discharge pipe line from the supply/discharge port in a case in which endoscopy is performed in a state in which a balloon is not mounted, brushing is necessary.

In the brushing of the supply/discharge pipe line, a cleaning brush is inserted into the supply/discharge pipe line from an operation unit side where an inlet of the supply/discharge pipe line is provided, and an operation for pushing and moving the cleaning brush toward the tip in the supply/discharge pipe line and an operation for drawing a brush portion of the cleaning brush back toward the operation unit are performed.

Since the supply/discharge port opens in a direction perpendicular to the axial direction of the insertion part in the ultrasonic endoscope in the related art, the supply/discharge pipe line provided along the axial direction of the insertion part is connected to the supply/discharge port in a state in which the supply/discharge pipe line is bent at a right angle or is bent obliquely. For this reason, when brushing is performed in the supply/discharge pipe line, the brush portion disposed at the tip of the cleaning brush cannot protrude from the supply/discharge port. Accordingly, there is a problem that liquid, residue, and the like entering the supply/discharge pipe line from the supply/discharge port cannot be sufficiently removed. Furthermore, since the supply/discharge pipe line has a very small diameter $\varphi$ of about 1.0 mm and a thin cleaning brush is also used, a large bending stress is applied to the cleaning brush at a bent portion of the supply/discharge pipe line when the bending angle of the supply/discharge pipe line is increased. For this reason, there is a case in which the cleaning brush may be subjected to bending damage.

In contrast, in an ultrasonic endoscope disclosed in, for example, JP2009-207758A, a tip surface is formed outside the profile of a tip unit-protruding portion where an ultrasonic observation unit is provided (unevenly thick portion side) and a supply/discharge port (a pipe line opening) of a supply/discharge pipe line (a pipe line for a balloon) is provided on the tip surface. According to this ultrasonic endoscope, since a brush portion of a cleaning brush may easily protrude from the supply/discharge port, liquid, residue, and the like present near the supply/discharge port can be efficiently removed by the cleaning brush. Further, since the pipe line for a balloon is connected to the pipe line opening at a gentle bending angle, bending damage to the cleaning brush can also be prevented.

SUMMARY OF THE INVENTION

However, in the ultrasonic endoscope disclosed in JP2009-207758A, in order to ensure a space in which the supply/discharge port is disposed, the tip surface needs to be formed outside the profile of the tip unit-protruding portion where the ultrasonic observation unit is provided (unevenly thick portion side) as described above, and the outer diameter of the tip portion of the insertion part needs to be large. For this reason, it is difficult to reduce the diameter and size of the tip portion of the insertion part, which causes the physical burden on a patient to be increased. Since the tip unit-protruding portion where the ultrasonic observation unit is provided needs to be made compact in order to dispose the supply/discharge port without changing the outer diameter of the tip portion of the insertion part, a space in which the ultrasonic observation unit is provided may be caused to be not sufficient.

Further, in a structure in which the supply/discharge port is exposed to the tip surface that is formed outside the profile of the tip unit-protruding portion, the balloon sticks on the supply/discharge port and closes the supply/discharge port when an ultrasonic transmission medium present in the balloon is discharged. For this reason, there is also a problem that the ultrasonic transmission medium cannot be discharged from the balloon.

The invention has been made in consideration of the above-mentioned circumstances, and an object of the invention is to provide an ultrasonic endoscope of which a supply/discharge pipe line can be efficiently cleaned with a cleaning brush while the diameter and size of a tip portion of an insertion part to be inserted into a body cavity are reduced.

In order to achieve the object, an ultrasonic endoscope according to an aspect of the invention comprises: an insertion part that includes a tip, a base end, and a longitudinal axis; an ultrasonic transducer that is provided at the tip of the insertion part; a balloon mounting portion which is disposed closer to the base end of the insertion part than the ultrasonic transducer is and on which a balloon wrapping the ultrasonic transducer is detachably mounted; a supply/discharge pipe line for a balloon that extends in the insertion part; a tip-side opening surface of the supply/discharge pipe line for a balloon, the tip-side opening surface being provided closer to the tip than the balloon mounting portion and having components normal to a direction of the longitudinal axis; and a groove portion which is formed toward the tip from the tip-side opening surface as a starting point and of which at least a part overlaps the ultrasonic transducer in the direction of the longitudinal axis.

According to this aspect, the tip-side opening surface of the supply/discharge pipe line for a balloon is provided closer to the tip than the balloon mounting portion and has components in the direction of the longitudinal axis of the insertion part, and the groove portion, which is formed toward the tip from the tip-side opening surface as a starting point and of which at least a part overlaps the ultrasonic transducer in the direction of the longitudinal axis, is provided. Accordingly, it is possible to allow the brush portion of the cleaning brush to protrude from the tip-side opening surface without applying excessive bending stress to the cleaning brush inserted into the supply/discharge pipe line for a balloon. Therefore, it is possible to efficiently perform the brushing of the supply/discharge pipe line for a balloon while reducing the size and diameter of the tip portion of the insertion part to be inserted into the body cavity.

In the ultrasonic endoscope according to the aspect of the invention, the groove portion includes a straight groove that extends from the tip-side opening surface in the direction of the longitudinal axis, and an inclined groove which extends from the straight groove so as to be inclined with respect to the direction of the longitudinal axis and of which a depth is gradually reduced toward the tip.

In the ultrasonic endoscope according to the aspect of the invention, a base end side of the groove portion extends toward the base end beyond the tip-side opening surface and the depth of the groove portion is reduced toward the base end.

In the ultrasonic endoscope according to the aspect of the invention, the groove portion is provided at any one of a pair of side wall portions that face each other with the ultrasonic transducer interposed therebetween.

In the ultrasonic endoscope according to the aspect of the invention, the groove portion is provided at a bottom wall portion from which a pair of side wall portions facing each other with the ultrasonic transducer interposed therebetween are erected.

In the ultrasonic endoscope according to the aspect of the invention, the groove portion extends up to a position that is closer to the base end than a tip surface of the insertion part.

In the ultrasonic endoscope according to the aspect of the invention, the groove portion extends up to a tip surface of the insertion part.

According to the invention, it is possible to efficiently clean a supply/discharge pipe line for a balloon with a cleaning brush while reducing the diameter and size of a tip portion of an insertion part to be inserted into a body cavity.

DESCRIPTION OF THE PREFERRED EMBODIMENTS

An ultrasonic endoscope according to a preferred embodiment of the invention will be described in detail below with reference to the accompanying drawings.

Figure 1:
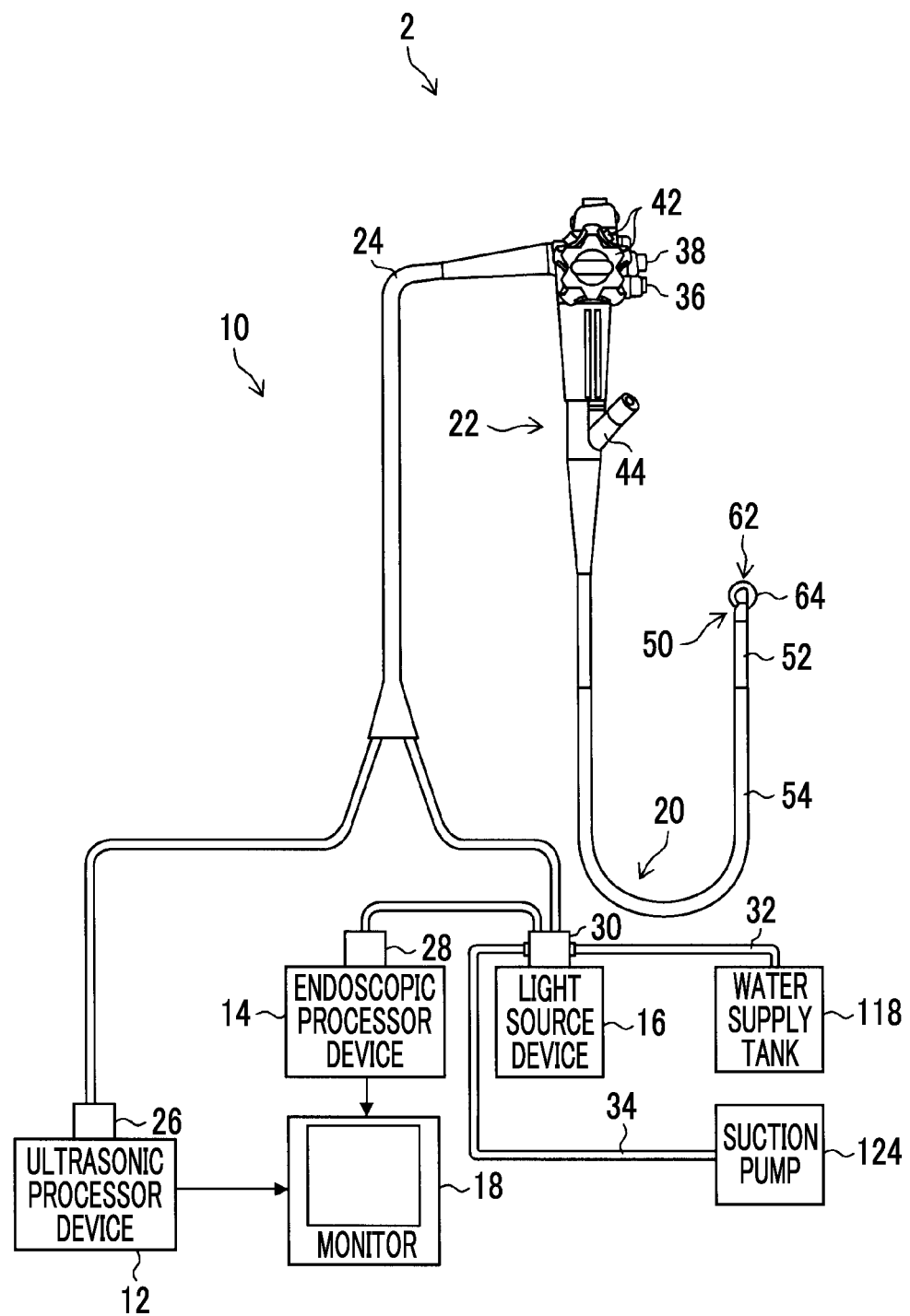
FIG. 1 is a schematic view showing the configuration of an ultrasonography system using an ultrasonic endoscope to which the invention is applied.

FIG. 1 is a schematic view showing the configuration of an ultrasonography system using an ultrasonic endoscope to which the invention is applied.

As shown in FIG. 1, an ultrasonography system 2 comprises an ultrasonic endoscope 10 that takes an image of the inside of a body cavity of a subject; an ultrasonic processor device 12 that generates an ultrasound image; an endoscopic processor device 14 that generates an endoscopic image; a light source device 16 that supplies illumination light, which illuminates the inside of the body cavity, to the ultrasonic endoscope 10; and a monitor 18 that displays the ultrasound image and the endoscopic image.

The ultrasonic endoscope 10 includes: an insertion part 20 that is to be inserted into the body cavity of a subject; an operation unit 22 that is connected to a base end portion of the insertion part 20 and is operated by an operator, such as a medical doctor or a technician; and a universal cord 24 of which one end is connected to the operation unit 22. The other end portion of the universal cord 24 is provided with an ultrasonic connector 26 that is connected to the ultrasonic processor device 12, an endoscope connector 28 that is connected to the endoscopic processor device 14, and a light source connector 30 that is connected to the light source device 16. The ultrasonic endoscope 10 is detachably connected to the ultrasonic processor device 12, the endoscopic processor device 14, and the light source device 16 through the respective connectors 26, 28, and 30. Further, a tube 32 for supplying air and water and a tube 34 for suction are connected to the light source connector 30.

The monitor 18 receives video signals that are generated by the ultrasonic processor device 12 and the endoscopic processor device 14 and displays the ultrasound image and the endoscopic image. In regard to the display of the ultrasound image and the endoscopic image, only one of the ultrasound image and the endoscopic image can be appropriately switched and displayed on the monitor 18, or both of the images can be simultaneously displayed. A monitor for displaying the ultrasound image and a monitor for displaying the endoscopic image may be separately provided. Alternatively, the ultrasound image and the endoscopic image may be displayed on one monitor.

The operation unit 22 is provided with an air supply/water supply button 36 and a suction button 38, which are arranged to be parallel, a pair of angle knobs 42 and 42, and a treatment tool insertion opening (forceps port) 44.

The insertion part 20 has a tip, a base end, and a longitudinal axis, and includes a tip portion (hard tip portion) 50, a bendable portion 52, and a soft portion 54 in this order from the tip side. The tip portion (hard tip portion) 50 is formed of a hard member. The bendable portion 52 is connected to a base end side of the tip portion 50 and can be bent. The soft portion 54 connects a base end side of the bendable portion 52 to a tip side of the operation unit 22, is thin and long, and has flexibility. The bendable portion 52 is remotely operated so as to be bent by the rotation of the pair of angle knobs 42 and 42 of the operation unit 22. Accordingly, the tip portion 50 can be directed in a desired direction. Further, a balloon 64 to be described below is detachably mounted on the tip portion 50.

Figure 2:
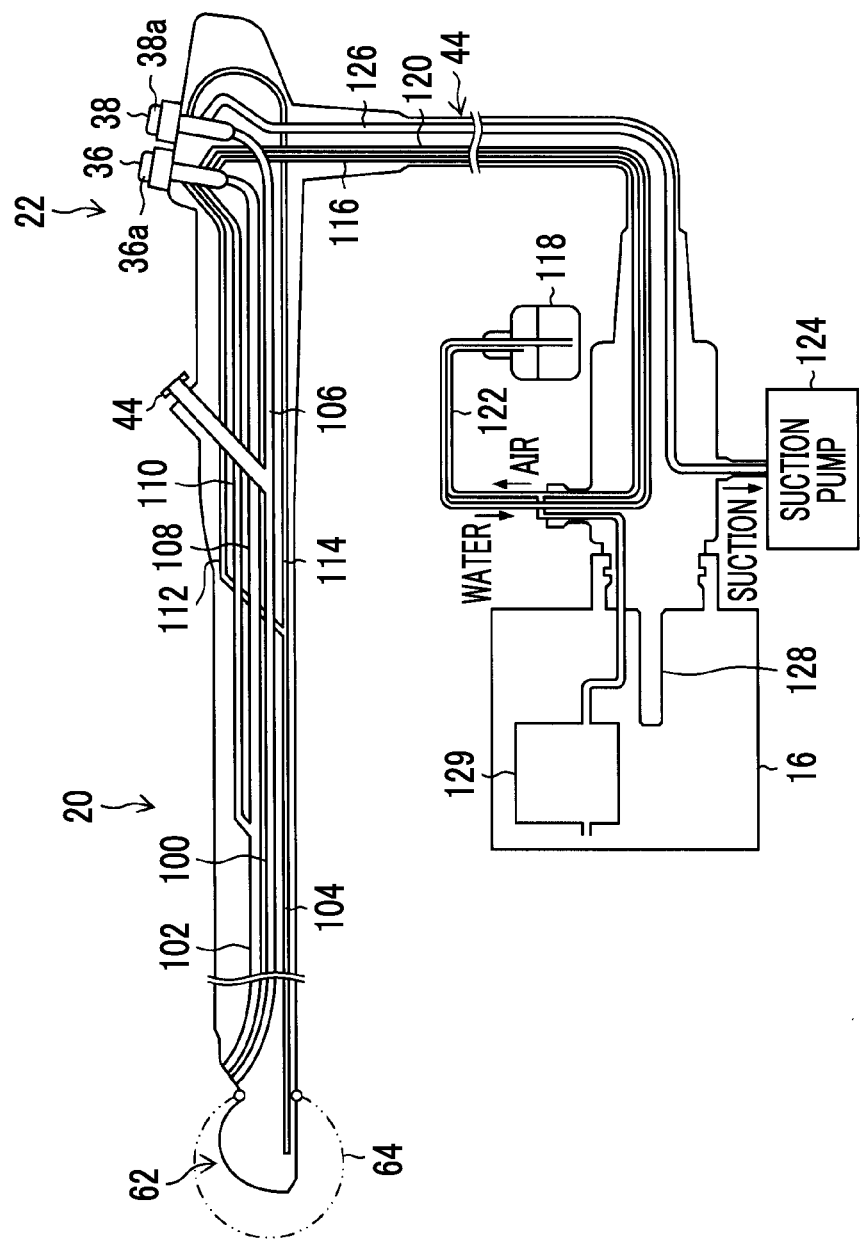
FIG. 2 is a view showing the configuration of pipe lines of the ultrasonic endoscope.

Here, the configuration of pipe lines of the ultrasonic endoscope 10 will be described. FIG. 2 is a view showing the configuration of pipe lines of the ultrasonic endoscope 10.

As shown in FIG. 2, a treatment tool channel 100, an air supply/water supply pipe line 102, and a balloon pipe line 104 of which one end communicates with the internal space of the balloon 64 are provided in the insertion part 20 and the operation unit 22. The balloon pipe line 104 is a form of a supply/discharge pipe line for a balloon of the invention.

One end of the treatment tool channel 100 is connected to a treatment tool outlet 94 (see FIG. 3) to be described below, and the other end thereof is connected to the treatment tool insertion opening 44 of the operation unit 22. The treatment tool insertion opening 44 is closed by a cover (not shown) except when a treatment tool is to be inserted. Further, a suction pipe line 106 is branched from the treatment tool channel 100, and the suction pipe line 106 is connected to the suction button 38 of the operation unit 22.

One end of the air supply/water supply pipe line 102 is connected to an air supply/water supply nozzle 92 (see FIG. 3) to be described below, and the other end thereof is branched into an air supply pipe line 108 and a water supply pipe line 110. The air supply pipe line 108 and the water supply pipe line 110 are connected to the air supply/water supply button 36 of the operation unit 22.

One end of the balloon pipe line 104 is connected to a supply/discharge port 70a that is provided closer to the tip than a balloon mounting portion to be described below, and the other end thereof is branched into a balloon water-supply pipe line 112 and a balloon drain pipe line 114. The balloon water-supply pipe line 112 is connected to the air supply/water supply button 36, and the balloon drain pipe line 114 is connected to the suction button 38.

One end of an air supply source pipe line 116, which communicates with an air supply pump 129, and one end of a water supply source pipe line 120, which communicates with a water supply tank 118, are connected to the air supply/water supply button 36 in addition to the air supply pipe line 108, the water supply pipe line 110, and the balloon water-supply pipe line 112. The air supply pump 129 is always operated during ultrasonic observation.

A branch pipe line 122 is branched from the air supply source pipe line 116, and the branch pipe line 122 is connected to an inlet of the water supply tank 118 (above the liquid level). Further, the other end of the water supply source pipe line 120 is inserted into the water supply tank 118 (below the liquid level). Then, when the internal pressure of the water supply tank 118 is increased by the supply of air from the air supply pump 129 through the branch pipe line 122, water present in the water supply tank 118 is supplied to the water supply source pipe line 120.

The air supply/water supply button 36 is a so-called two-stage switching button. Although not shown, an air outlet, which communicates with the atmosphere, is formed at an operation cap 36a of the air supply/water supply button. When the operation cap 36a is not operated, the air supply/water supply button 36 allows the water supply source pipe line 120 to be closed and allows the air supply source pipe line 116 to communicate with the air outlet of the operation cap 36a. Accordingly, air, which is supplied from the air supply source pipe line 116, leaks from the air outlet of the air supply/water supply button 36. Then, when the air outlet is closed in this state, the air supply source pipe line 116 and the air supply pipe line 108 communicate with each other in a state in which the water supply source pipe line 120 continues to be closed. Accordingly, air is supplied to the air supply pipe line 108 and is ejected to the outside from the air supply/water supply nozzle 92.

Furthermore, when the operation cap 36a is halfway push-operated, the air supply/water supply button 36 allows the air supply source pipe line 116 to be closed and allows the water supply source pipe line 120 to communicate with only the water supply pipe line 110. Accordingly, water supplied from the water supply source pipe line 120 is ejected from the air supply/water supply nozzle 92 through the water supply pipe line 110 and the like. Then, when the operation cap 36a is fully push-operated, the air supply/water supply button 36 allows the water supply source pipe line 120 to communicate with only the balloon water-supply pipe line 112 in a state in which the air supply source pipe line 116 continues to be closed. Accordingly, water, which is supplied from the water supply source pipe line 120, is supplied into the balloon 64 through the balloon water-supply pipe line 112 and the like.

The other end of a suction source pipe line 126 of which one end communicates with a suction pump 124 is connected to the suction button 38 in addition to the suction pipe line 106 and the balloon drain pipe line 114. The suction pump 124 is also always operated during ultrasonic observation. The suction button 38 is a two-stage switching button like the air supply/water supply button 36.

When an operation cap 38a of the suction button 38 is not operated, the suction button 38 allows the suction source pipe line 126 to communicate with the outside (the atmosphere). The reason for this is that a load applied to the suction pump 124 is increased unless the suction source pipe line 126 communicates with the atmosphere since the suction pump 124 is always operated. When the suction source pipe line 126 is allowed to communicate with the atmosphere, an increase of the load of the suction pump 124 is suppressed.

Further, when the operation cap 38a is halfway push-operated, the suction button 38 allows the suction source pipe line 126 to communicate with only the suction pipe line 106. Accordingly, a negative pressure-suction force of the suction pipe line 106 and the treatment tool channel 100 is increased, and various materials to be sucked are sucked from the treatment tool outlet 94 (see FIG. 3). Then, when the operation cap 38a is fully push-operated, the suction button 38 allows the suction source pipe line 126 to communicate with only the balloon drain pipe line 114. Accordingly, a negative pressure-suction force in the balloon drain pipe line 114 and the balloon pipe line 104 is increased, and water present in the balloon 64 is drained.

Figure 3:
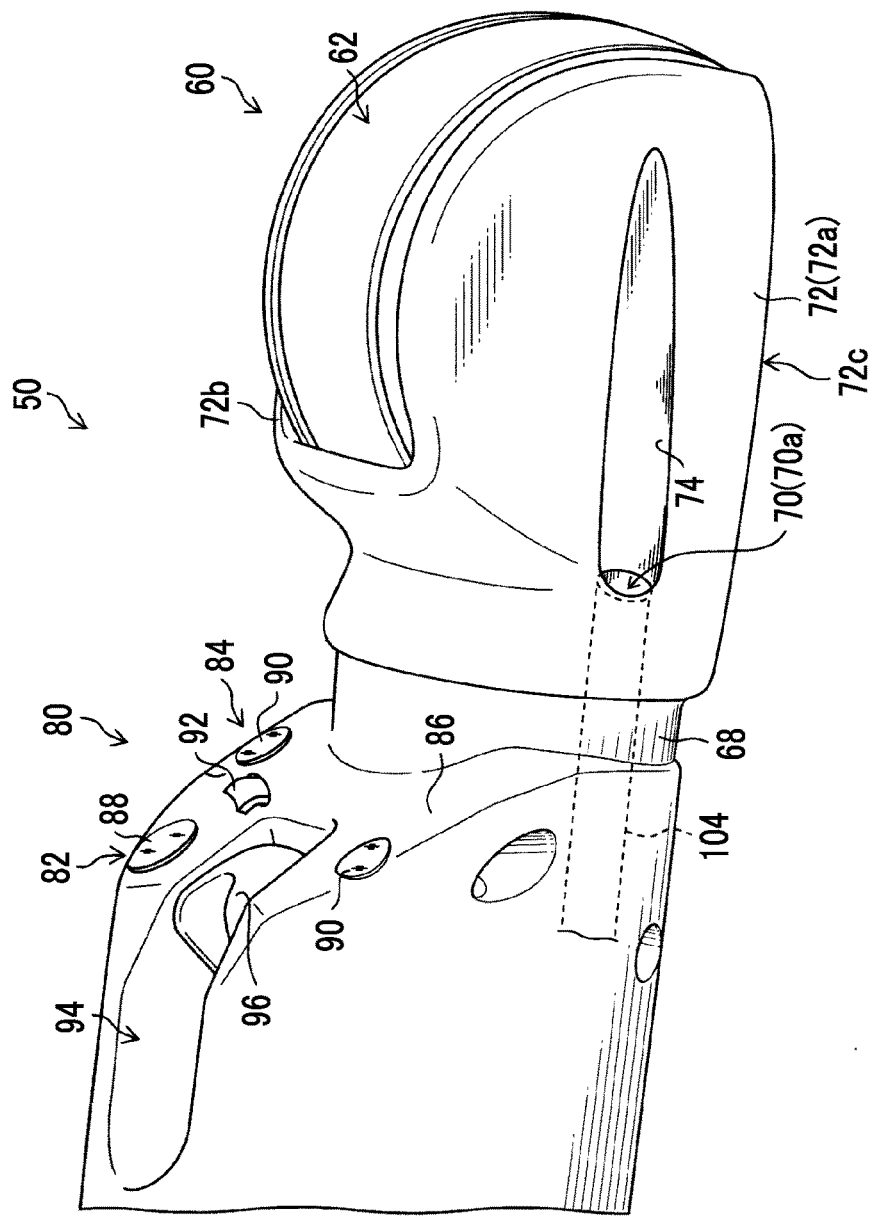
FIG. 3 is a perspective view of a tip portion of an insertion part of the ultrasonic endoscope.

Next, the structure of the tip portion 50 of the ultrasonic endoscope 10 will be described in detail. FIG. 3 is a perspective view of the tip portion 50, FIG. 4 is a side view of the tip portion 50, and FIG. 5 is a plan view (a partial sectional view) of the tip portion 50.

Figure 4:
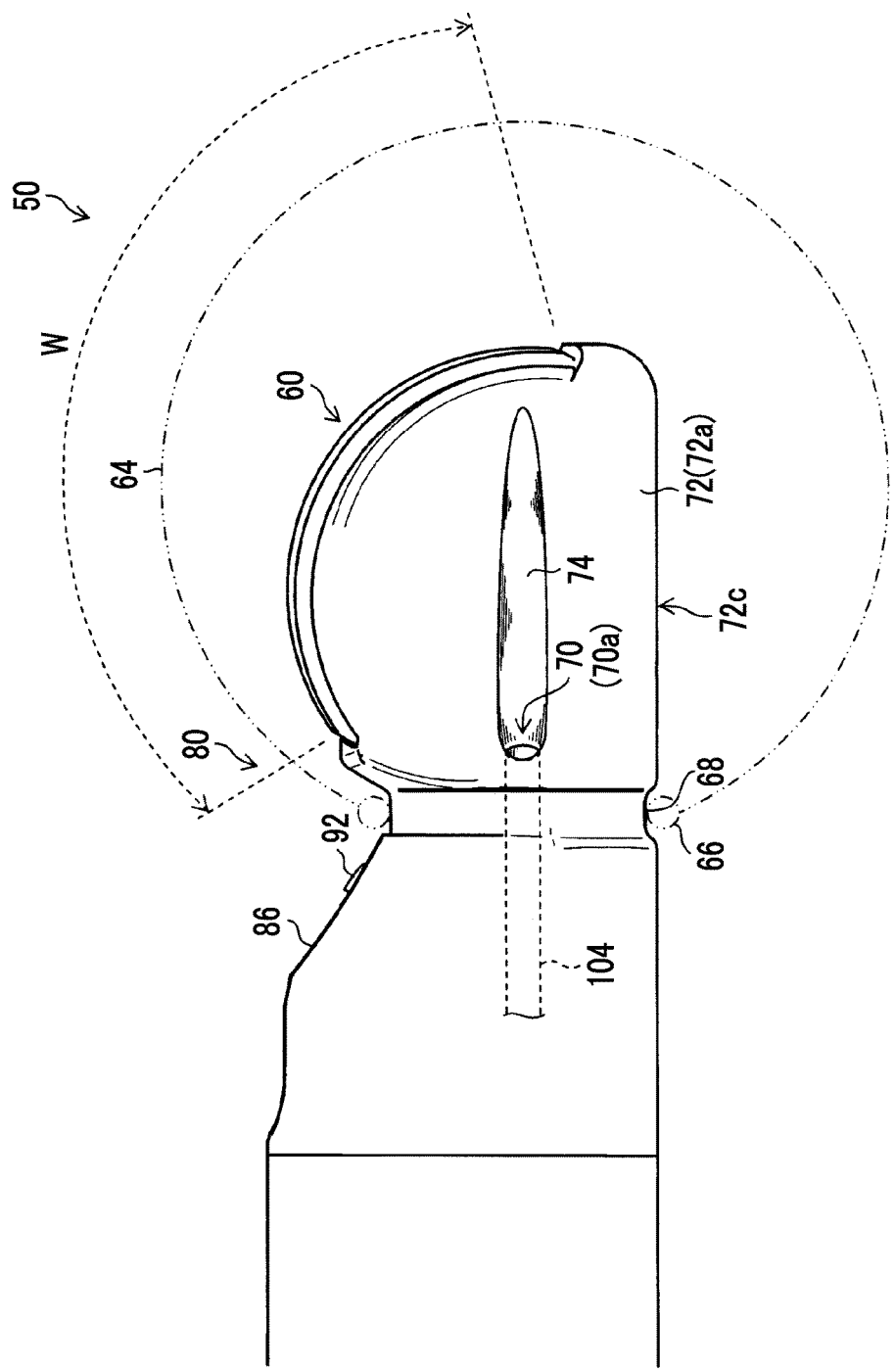
FIG. 4 is a side view of the tip portion of the insertion part of the ultrasonic endoscope.
Figure 5:
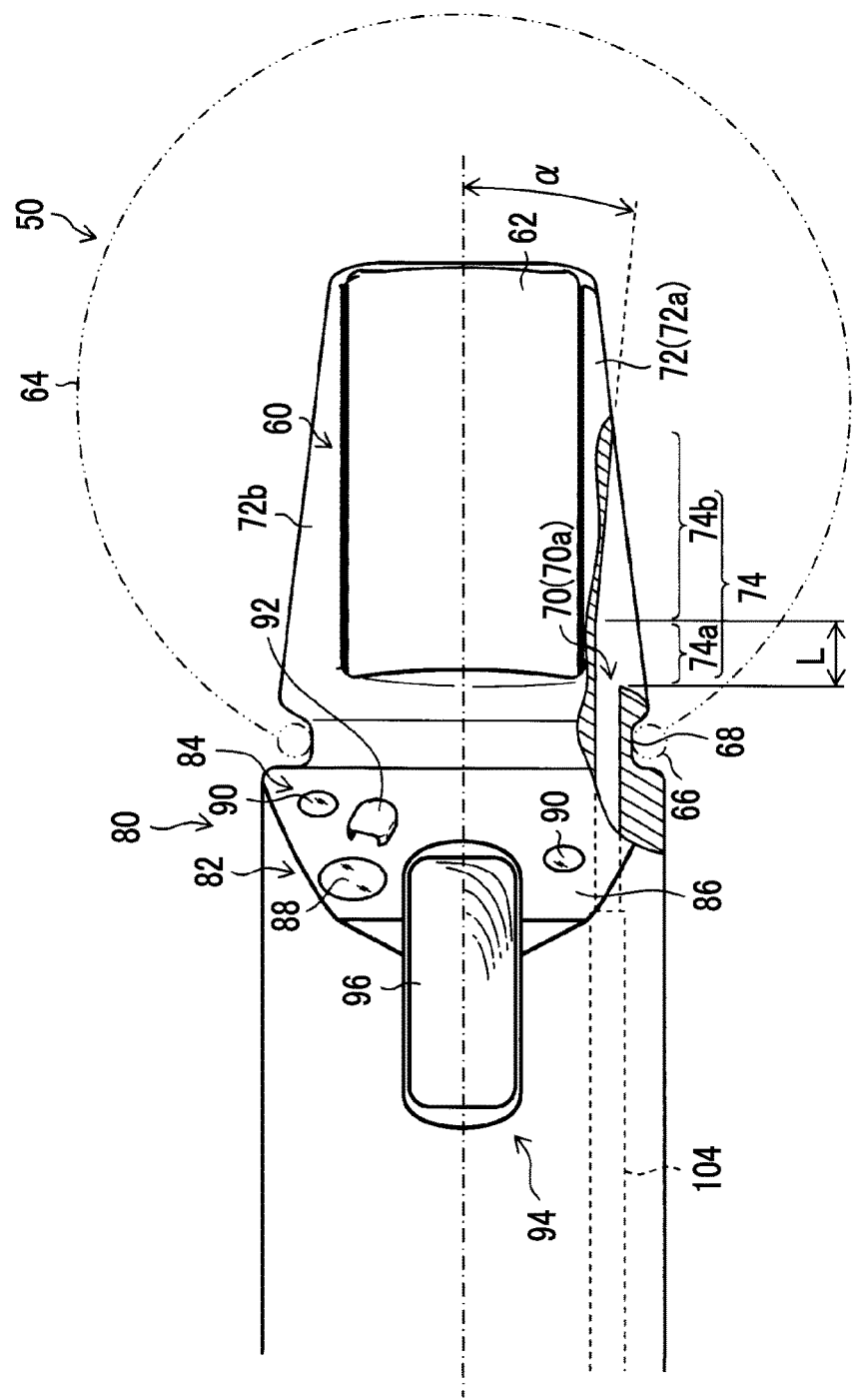
FIG. 5 is a plan view (a partial sectional view) of the tip portion of the insertion part of the ultrasonic endoscope.

As shown in FIGS. 3 to 5, an ultrasonic observation unit 60 that acquires an ultrasound image and the endoscopic observation unit 80 that acquires an endoscopic image are provided at the tip portion 50 of the ultrasonic endoscope 10.

The ultrasonic observation unit 60 comprises an ultrasonic transducer 62 that includes a plurality of ultrasonic vibrators. The respective ultrasonic vibrators of the ultrasonic transducer 62 are arranged at regular intervals in the shape of a convex curve along the axial direction of the tip portion 50 (a direction of the longitudinal axis of the insertion part 20), and are adapted to be sequentially driven on the basis of drive signals that are input from the ultrasonic processor device 12. Accordingly, convex electronic scanning is performed over a scanning range shown in FIG. 4 by W. When the respective ultrasonic vibrators are driven, the ultrasonic vibrators sequentially generate ultrasonic waves toward a portion to be observed, receive ultrasonic echoes (echo signals) reflected by the portion to be observed, and output electrical signals (ultrasonic wave-detection signals), which correspond to the received ultrasonic echoes, to the ultrasonic processor device 12. Then, after various kinds of signal processing are performed in the ultrasonic processor device 12, the electrical signals are displayed on the monitor 18 as the ultrasound image.

A bag-shaped balloon 64, which covers and wraps the ultrasonic transducer 62, is mounted on the tip portion 50 in order to prevent the attenuation of the ultrasonic waves and the ultrasonic echoes (echo signals) (see FIGS. 4 and 5). The balloon 64 is made of a stretchable elastic material, and a stretchable locking ring 66 is formed at an open end of the balloon 64. A locking groove 68, which forms a balloon mounting portion, is provided at the tip portion 50. The locking groove 68 is formed of an annular groove portion that is formed over the entire circumference (outer periphery) of the tip portion 50 in a circumferential direction having a center on the axis. The locking ring 66 is fitted to the locking groove 68, so that the balloon 64 is detachably mounted on the tip portion 50.

The balloon 64 is inserted into the body cavity in a state in which the balloon 64 contracts so as to come into close contact with the outer wall surface of the tip portion 50. Then, when an operator generates ultrasonic waves toward the portion to be observed from the respective ultrasonic vibrators of the ultrasonic transducer 62, the operator supplies water, which is present in the water supply tank 118, into the balloon 64 through the balloon pipe line 104, the balloon water-supply pipe line 112, and the like by fully push-operating the operation cap 36a of the air supply/water supply button 36 and inflates the balloon 64 until the balloon 64 comes into contact with the inner wall of the body cavity. Accordingly, since a space between the portion to be observed and the ultrasonic transducer 62 is filled with water that is an ultrasonic transmission medium, the balloon 64 improves the adhesiveness of the tip portion 50 to the inner wall of the body cavity and prevents the ultrasonic waves, which are generated from the respective ultrasonic vibrators of the ultrasonic transducer 62, and the ultrasonic echoes from being attenuated by air. Further, when an operator draws the insertion part 20 to the outside from the body cavity, the operator discharges water, which is present in the balloon 64, through the balloon pipe line 104, the balloon drain pipe line 114, and the like by fully push-operating the operation cap 38a of the suction button 38 and allows the balloon 64 to contract so that the balloon 64 comes into close contact with the outer wall surface of the tip portion 50 as when the operator inserts the insertion part 20 into the body cavity. For example, latex rubber is used for the balloon 64. Further, it is preferable that the ultrasonic transmission medium supplied into the balloon 64 is deaerated water from which dissolved gas has been removed.

The balloon pipe line 104 as the supply/discharge pipe line for a balloon extends in the insertion part 20 as described above, and a tip-side opening surface 70, which has components normal to the direction of the longitudinal axis of the insertion part 20 (the axial direction of the tip portion 50), is provided at the tip of the balloon pipe line 104. The tip-side opening surface 70 is provided closer to the tip than the locking groove 68 that forms the balloon mounting portion, and includes a supply/discharge port 70a that is opened at one end (tip) of the balloon pipe line 104.

A housing member (exterior member) 72, which holds the ultrasonic transducer 62, is provided with a groove portion 74 (having a notched shape) that is formed by notching a part of the outer wall of the housing member. The groove portion 74 is formed toward the tip from the tip-side opening surface 70 as a starting point, and is formed so that at least a part of the groove portion 74 overlaps the ultrasonic transducer 62 in the direction of the longitudinal axis of the insertion part 20.

A structure in which the groove portion 74 is provided at a left side wall portion 72a of a pair of side wall portions 72a and 72b, which face each other with the ultrasonic transducer 62 interposed therebetween, of an outer wall portion of the housing member 72 when the tip portion 50 is viewed from the tip side has been described in the embodiment shown in FIGS. 3 to 5. However, the invention is not limited thereto, and the groove portion 74 may be provided at a right side wall portion 72b or a bottom wall portion 72c from which these side wall portions 72a and 72b are erected, as described below.

Here, the structure of the groove portion 74 will be described in more detail. The groove portion 74, which is formed toward the tip from the tip-side opening surface 70 as a starting point, extends to the near side (the base end side) of a tip surface of the tip portion 50 as shown in FIG. 5. The groove portion 74 includes a straight groove 74a and an inclined groove 74b in this order from the base end side (a side where the tip-side opening surface 70 is formed).

The straight groove 74a extends from the tip-side opening surface 70 in the direction of the longitudinal axis of the insertion part 20, and includes a bottom surface parallel to the direction of the longitudinal axis of the insertion part 20. The straight groove 74a does not bend a brush portion, which is provided at the tip of a cleaning brush led out from the supply/discharge port 70a of the tip-side opening surface 70, and guides the brush portion in the axial direction of the balloon pipe line 104. It is preferable that the length L (see FIG. 5) of the straight groove 74a is 1 mm or more, and the length L is 1.5 mm in this embodiment. If the length L is set to this length, it is possible to allow the brush portion of the cleaning brush to protrude from the supply/discharge port 70a without applying excessive stress to the brush portion of the cleaning brush.

The inclined groove 74b extends from the straight groove 74a so as to be inclined with respect to the direction of the longitudinal axis of the insertion part 20, and the depth of the groove is gradually reduced toward the tip. That is, the inclined groove 74b includes a bottom surface that is formed so as to be inclined with respect to the normal direction of the tip-side opening surface 70 (the opening direction of the supply/discharge port 70a). Accordingly, when the brush portion of the cleaning brush, which protrudes from the supply/discharge port 70a, is further pushed and moved toward the tip, the brush portion of the cleaning brush is guided in a direction in which the brush portion is separated from the ultrasonic transducer 62 and is in a state in which the brush portion is drawn to the outside (the lateral side) from the outer wall surface of the housing member 72. Therefore, the brush portion of the cleaning brush can be easily washed with a hand. When an inclination angle α (see FIG. 5) of the inclined groove 74b is too large, excessive stress is applied to the brush portion of the cleaning brush. Accordingly, it is preferable that the inclination angle α is at least 45° or less, and the inclination angle α is 10° in this embodiment.

Particularly, in this embodiment, the groove portion 74 (having a notched shape) is formed by notching a part of the outer wall of the housing member 72 arranged to be parallel to the ultrasonic transducer 62, that is, the groove portion 74 is formed so that at least a part of the groove portion 74 overlaps the ultrasonic transducer 62 in the direction of the longitudinal axis of the insertion part 20. Accordingly, it is possible to sufficiently ensure the length of the groove portion 74 (the length of the groove portion 74 in the direction of the longitudinal axis of the insertion part 20) without increasing the size of the tip portion 50 in the axial direction, and to make the inclination angle α of the inclined groove 74b be gentler. Therefore, since excessive stress is not applied to the brush portion of the cleaning brush that is guided to the lateral side of the housing member 72 by the inclined groove 74b, it is possible to prevent a bending damage to cleaning brush.

The endoscopic observation unit 80 includes an observation portion 82 and an illumination portion 84, and the observation portion 82 and the illumination portion 84 are disposed on an inclined surface portion 86 that is formed on the tip portion 50 toward the base end from the locking groove 68 so as to be inclined with respect to the axial direction of the tip portion 50.

The observation portion 82 includes an observation window 88; and an objective lens of an observation optical system, and an imaging element, such as a Charge Coupled Device (CCD) or a Complementary Metal Oxide Semiconductor (CMOS), which is disposed at an image formation position of the objective lens, are provided in the rear of the observation window 88. A signal cable (not shown) is connected to a board that supports the imaging element. The signal cable is inserted into the insertion part 20 and the universal cord 24, extends up to the endoscope connector 28, and is connected to the endoscopic processor device 14. An observation image, which is received from the observation window 88, is formed on the light-receiving surface of the imaging element and is converted to an electrical signal (an imaging signal), and the electrical signal is output to the endoscopic processor device 14 through the signal cable and is converted to a video signal. Then, the video signal is output to the monitor 18 connected to the endoscopic processor device 14, so that an endoscopic image is displayed on a screen of the monitor 18.

The illumination portion 84 includes illumination windows 90 and 90, and a light-emitting end of a light guide 128 (see FIG. 2) is disposed in the rear of the illumination windows 90 and 90. The light guide 128 is inserted into the insertion part 20 and the universal cord 24 and an incident end of the light guide 128 is disposed in the light source connector 30. Accordingly, the light source connector 30 is connected to the light source device 16, so that illumination light emitted from the light source device 16 is transmitted to the illumination windows 90 and 90 through the light guide and is emitted forward from the illumination windows 90 and 90.

The air supply/water supply nozzle 92 is provided near the observation window 88 on the inclined surface portion 86 of the tip portion 50 in addition to the observation window 88 and the illumination windows 90 and 90. The air supply/water supply nozzle 92 ejects water or air to remove foreign materials and the like adhered to the surface of the observation window 88.

Further, the tip portion 50 is provided with a treatment tool outlet 94. The treatment tool outlet 94 is connected to the treatment tool channel 100 (see FIG. 2) inserted into the insertion part 20, and a treatment tool, which is inserted into the treatment tool insertion opening 44, is introduced into the body cavity from the treatment tool outlet 94 through the treatment tool channel 100. The treatment tool outlet 94 is positioned closer to the base end than the locking groove 68, but may be provided close to the ultrasonic transducer 62 so that the movement of the treatment tool introduced into the body cavity from the treatment tool outlet 94 can be confirmed by an ultrasound image.

An elevator 96 for making the lead-out direction of the treatment tool, which is introduced into the body cavity from the treatment tool outlet 94, be variable is provided in the treatment tool outlet 94. A wire (not shown) is mounted on the elevator 96, and the elevating angle of the elevator 96 is changed by a pushing/drawing operation that is performed by the operation of an elevating lever (not shown) of the operation unit 22. Accordingly, the treatment tool is led out in a desired direction.

Figure 6:
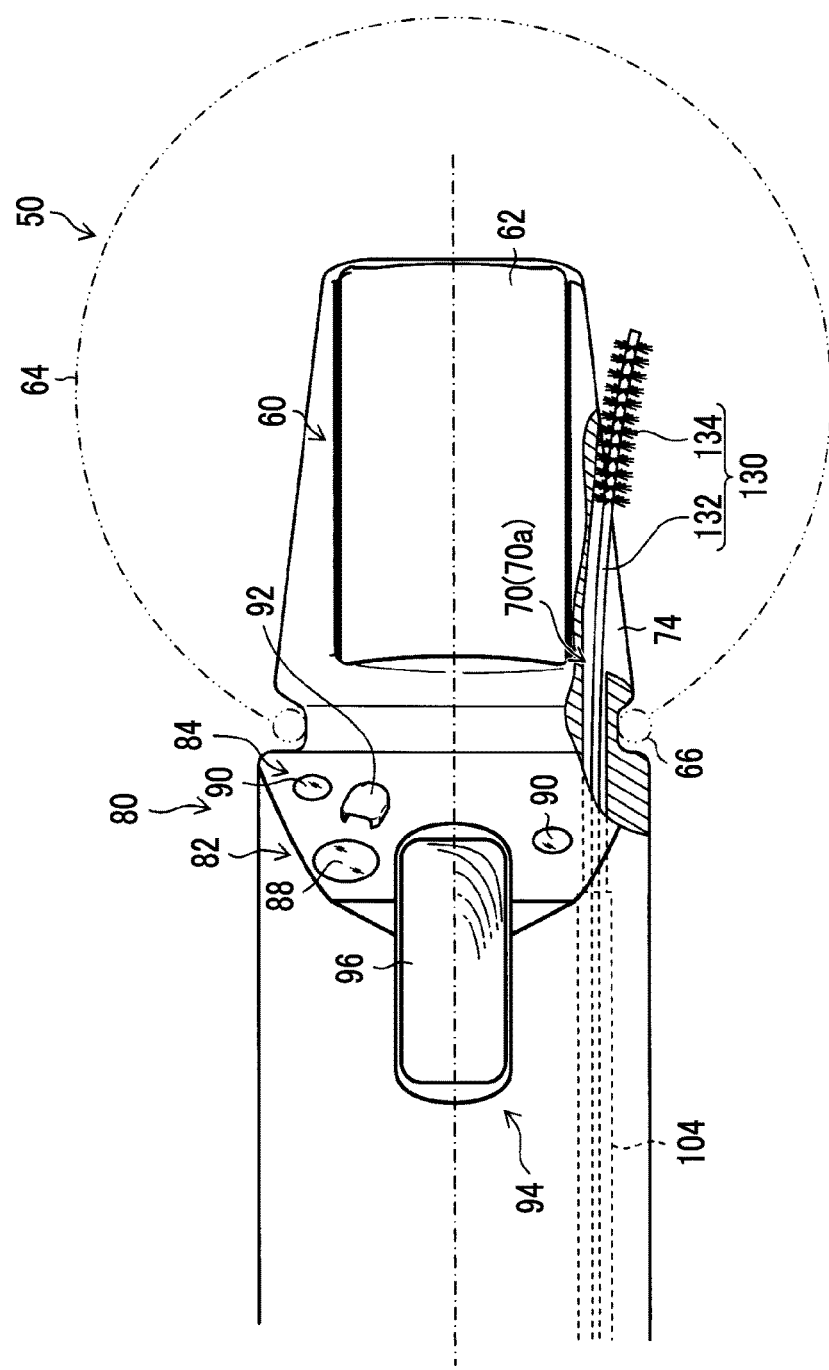
FIG. 6 is a view showing a state in which a supply/discharge pipe line is brushed.

In the ultrasonic endoscope 10 having the above-mentioned structure, the brushing of the balloon pipe line 104 is performed as follows after the end of endoscopy. FIG. 6 is a view showing a state in which the balloon pipe line 104 is brushed by using the cleaning brush. As shown in FIG. 6, a cleaning brush 130 includes a brush insertion part 132 and a brush portion 134 that is disposed at the tip portion of the brush insertion part 132.

First, after the balloon 64 is removed from the tip portion 50 of the insertion part 20, the cleaning brush 130 is inserted from the suction button 38 side that is an inlet of the balloon pipe line 104. Then, while the cleaning brush 130 inserted into the balloon drain pipe line 114 of the balloon pipe line 104 is moved forward and backward, the cleaning brush 130 is pushed and moved toward the tip and the brush portion 134 of the cleaning brush 130 is allowed to protrude from the supply/discharge port 70a that is an outlet of the balloon pipe line 104. The cleaning brush 130 may be inserted from the air supply/water supply button 36 side.

Then, when the brush portion 134 of the cleaning brush 130 is further pushed and moved, the brush portion 134 of the cleaning brush 130 is offset in a direction in which the brush portion 134 is separated from the axis of the tip portion 50 by the inclined groove 74b after the brush portion 134 of the cleaning brush 130 is guided in the same direction as the direction of the longitudinal axis of the insertion part 20 (that is, the axial direction of the balloon pipe line 104) by the straight groove 74a.

In this case, since the groove portion 74 (having a notched shape) is formed by notching a part of the outer wall of the housing member 72 arranged to be parallel to the ultrasonic transducer 62 in this embodiment as described above, it is possible to sufficiently ensure the length of the groove portion 74 (the length of the groove portion 74 in the axial direction of the tip portion 50) without increasing the size of the tip portion 50 and to make the inclination angle α (see FIG. 5) of the inclined groove 74b be gentler. For this reason, since excessive stress is not applied to the brush portion 134, it is possible to prevent a bending damage to the cleaning brush 130. Accordingly, it is possible to easily draw the brush portion 134 of the cleaning brush 130 to the lateral side of the tip portion 50. Therefore, the brush portion 134 can be easily washed with a hand.

Further, when the brush portion 134 of the cleaning brush 130 is washed with a hand, a user determines the degree of contamination of the brush portion 134. In a case in which it is determined that the brushing of the balloon pipe line 104 is further needed, the user removes the cleaning brush 130 from the suction button 38 side, washes the brush portion 134 with a hand again, and determines the degree of contamination of the brush portion 134 after the user performs the brushing of the balloon pipe line 104 while performing an operation for drawing the cleaning brush 130 back. Then, in a case in which it is determined that the brushing of the balloon pipe line 104 is further needed, the user inserts the cleaning brush 130 from the suction button 38 side and repeatedly performs the same processing as described above.

In a case in which the brushing of the balloon pipe line 104 is performed as described above and a fact that the balloon pipe line 104 is in a clean state is determined from the degree of contamination of the brush portion 134 of the cleaning brush 130, the brushing ends.

As described above, according to this embodiment, the tip-side opening surface 70 of the balloon pipe line 104, which forms the supply/discharge pipe line for a balloon, is provided closer to the tip than the locking groove 68 that is the balloon mounting portion, includes components in the direction of the longitudinal axis of the insertion part 20, and is provided with the groove portion 74, which is formed toward the tip from the tip-side opening surface 70 as a starting point and of which at least a part overlaps the ultrasonic transducer 62 in the direction of the longitudinal axis. Accordingly, it is possible to provide the groove portion 74 without increasing the size of the tip portion 50 in the direction of the longitudinal axis of the insertion part 20, and to sufficiently ensure the length of the groove portion 74. Therefore, since it is possible to allow the brush portion of the cleaning brush to protrude from the supply/discharge port 70a without applying excessive bending stress to the cleaning brush inserted into the balloon pipe line 104, it is possible to easily remove liquid, residue, and the like adhered to the vicinity of the supply/discharge port 70a. As a result, it is possible to efficiently perform the brushing of the balloon pipe line 104 while reducing the size and diameter of the tip portion 50 of the insertion part 20.

Figure 7:
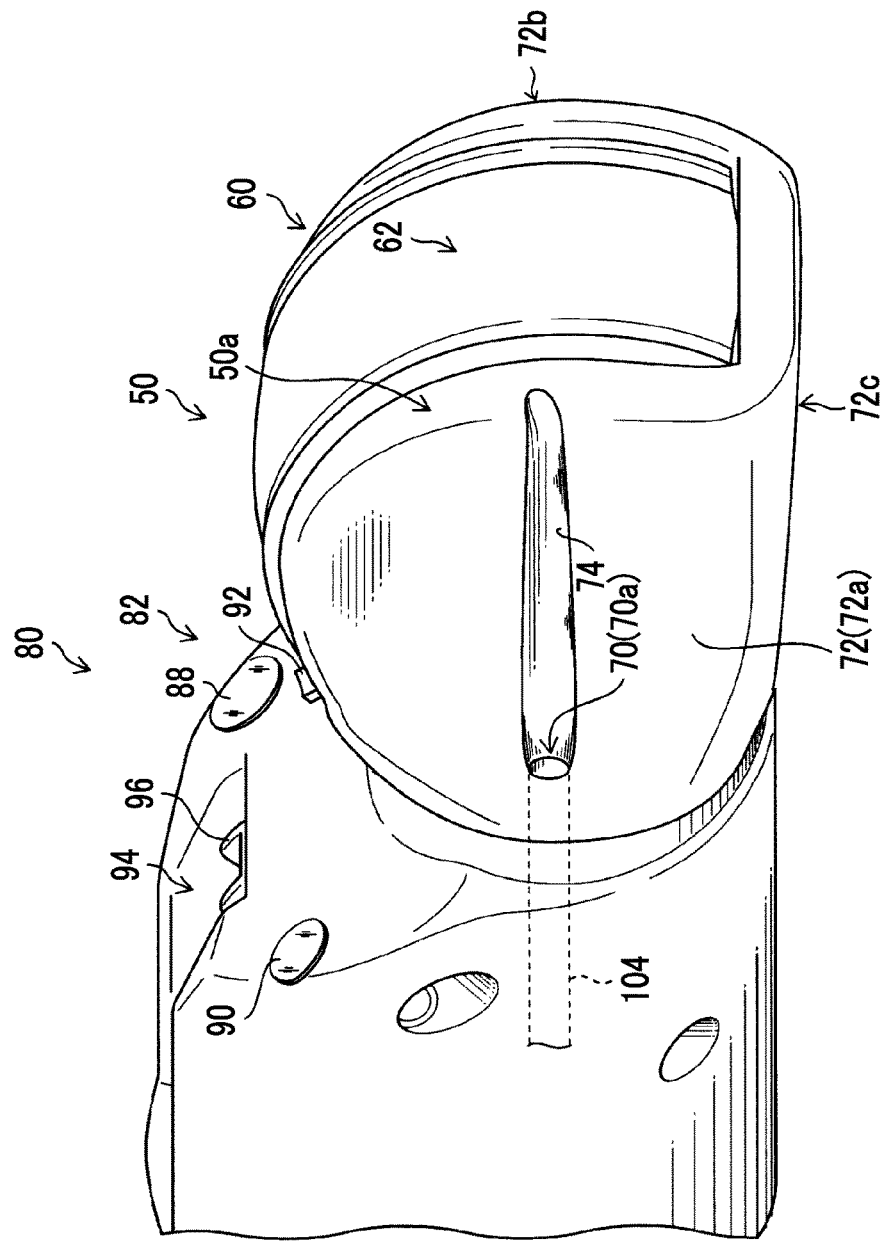
FIG. 7 is a view showing another example of the structure of a groove portion formed at a housing member.

In this embodiment, as shown in FIGS. 3 to 5, the groove portion 74 is formed at a position, which is closer to the base end than the tip surface 50a of the tip portion 50, so as to converge. However, the invention is not limited thereto, and the groove portion 74 may be formed so as to extend up to the tip surface 50a of the tip portion 50 as shown in, for example, FIG. 7. According to a structure that includes a groove portion 74 opened to the tip surface 50a, since the length of the groove portion 74 is longer than that of the structure shown in FIGS. 3 to 5, it is possible to make the inclination angle α (see FIG. 5) of the inclined groove 74b be gentler. Accordingly, it is possible to more effectively prevent a bending damage to the cleaning brush. It is preferable that the inclination angle α of the inclined groove 74b is in the range of 5° to 10°, and the inclination angle α of the inclined groove 74b is set to, for example, 7.5°.

Further, since the groove portion 74 is opened to the tip surface 50a of the tip portion 50, an effect of allowing the balloon 64 to reliably contract is also obtained even if the balloon 64 sticks on the side surface of the tip portion 50 when an ultrasonic transmission medium present in the balloon 64 is discharged.

According to the structure in which the groove portion 74 is formed at a position closer to the base end than the tip surface 50a of the tip portion 50 so as to converge as shown in FIGS. 3 to 5, it is possible to smoothly machine the tip surface 50a of the tip portion 50. Accordingly, it is possible to improve the insertability of the insertion part 20 of the ultrasonic endoscope 10 into the body cavity.

Figure 8:
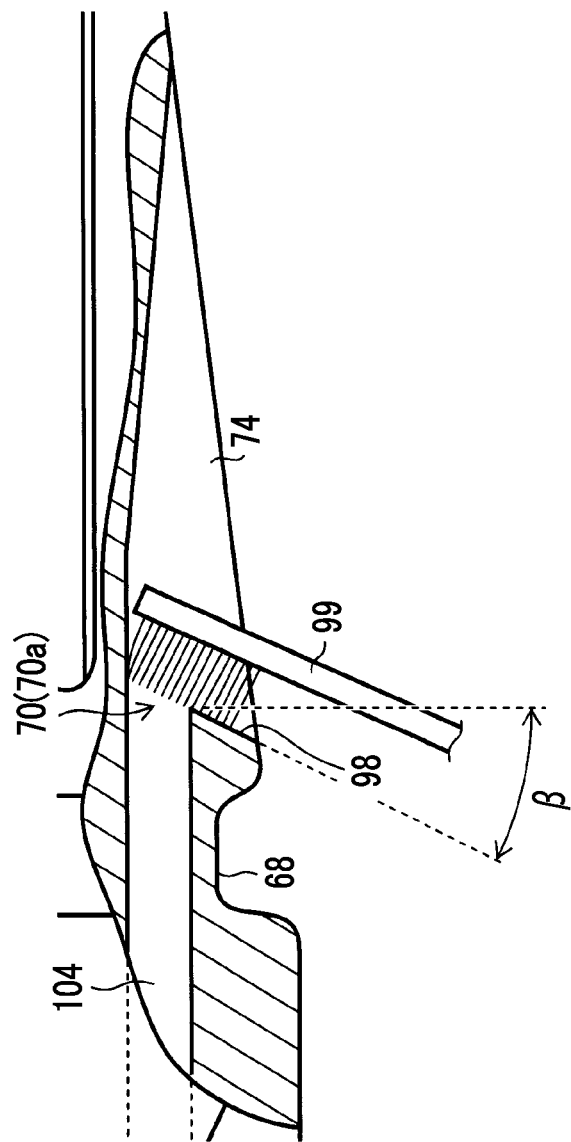
FIG. 8 is a view showing a state in which contamination near a supply/discharge port is removed by a brush.

Furthermore, it is preferable that the base end side of the groove portion 74 extends toward the base end beyond the tip-side opening surface and the depth of the groove is reduced toward the base end as shown in FIG. 8 enlarging the vicinity of the supply/discharge port 70a in FIG. 5. It is preferable that an inclination angle β of a base end-side inclined surface 98 of the groove portion 74 (the inclination angle of the base end-side inclined surface 98 with respect to a direction perpendicular to the direction of the longitudinal axis of the insertion part 20) is in the range of 10° to 45°, and the inclination angle β is, for example, 30°. If the groove portion 74 has a shape extending outward toward the base end in this way, it is possible to easily scrape off contaminations that are present near the supply/discharge port 70a when the groove portion 74 is brushed with a brush 99 for a groove portion.

Figure 9:
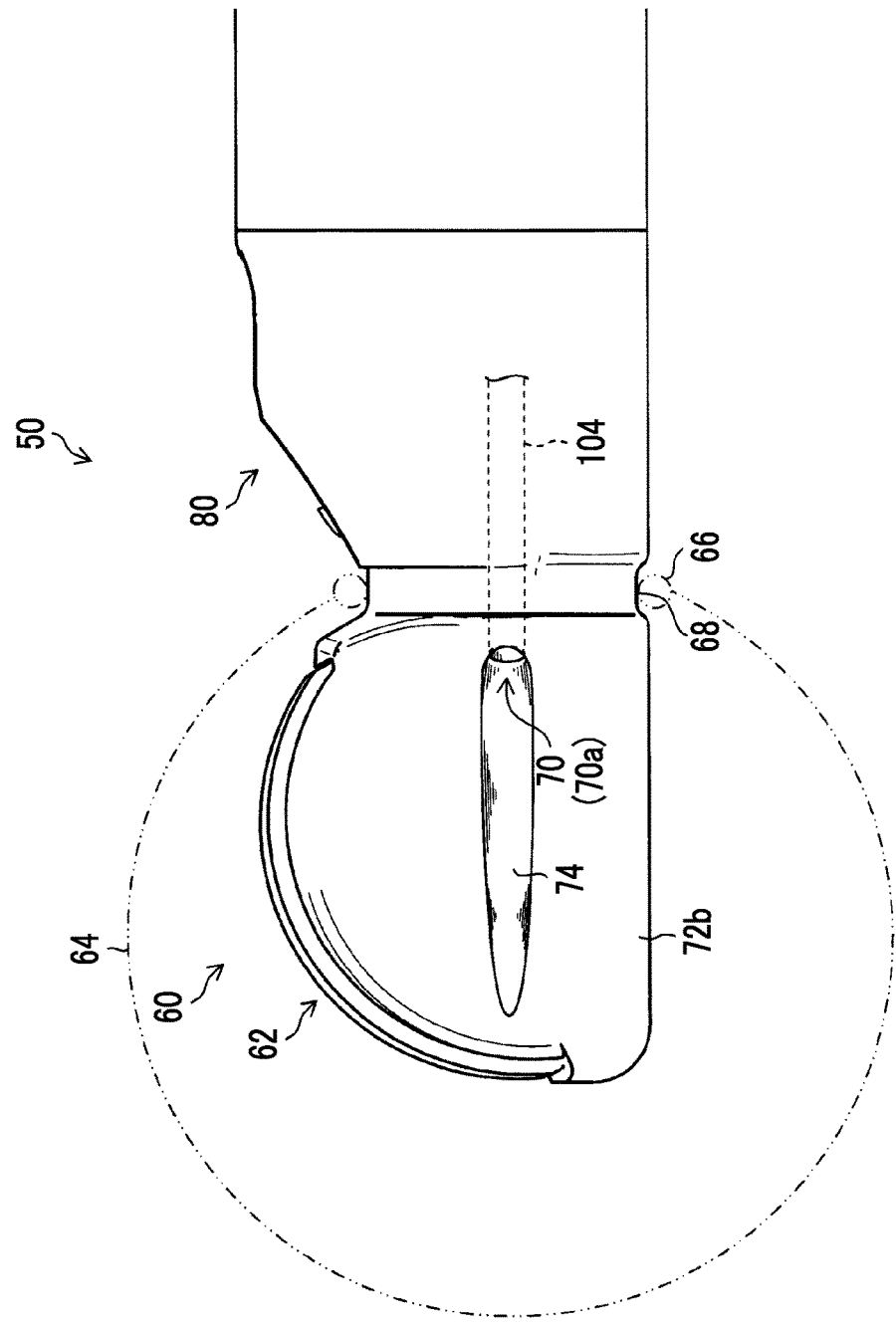
FIG. 9 is a view showing a structure in which a groove portion is formed on a right side wall portion of the housing member.
Figure 10:
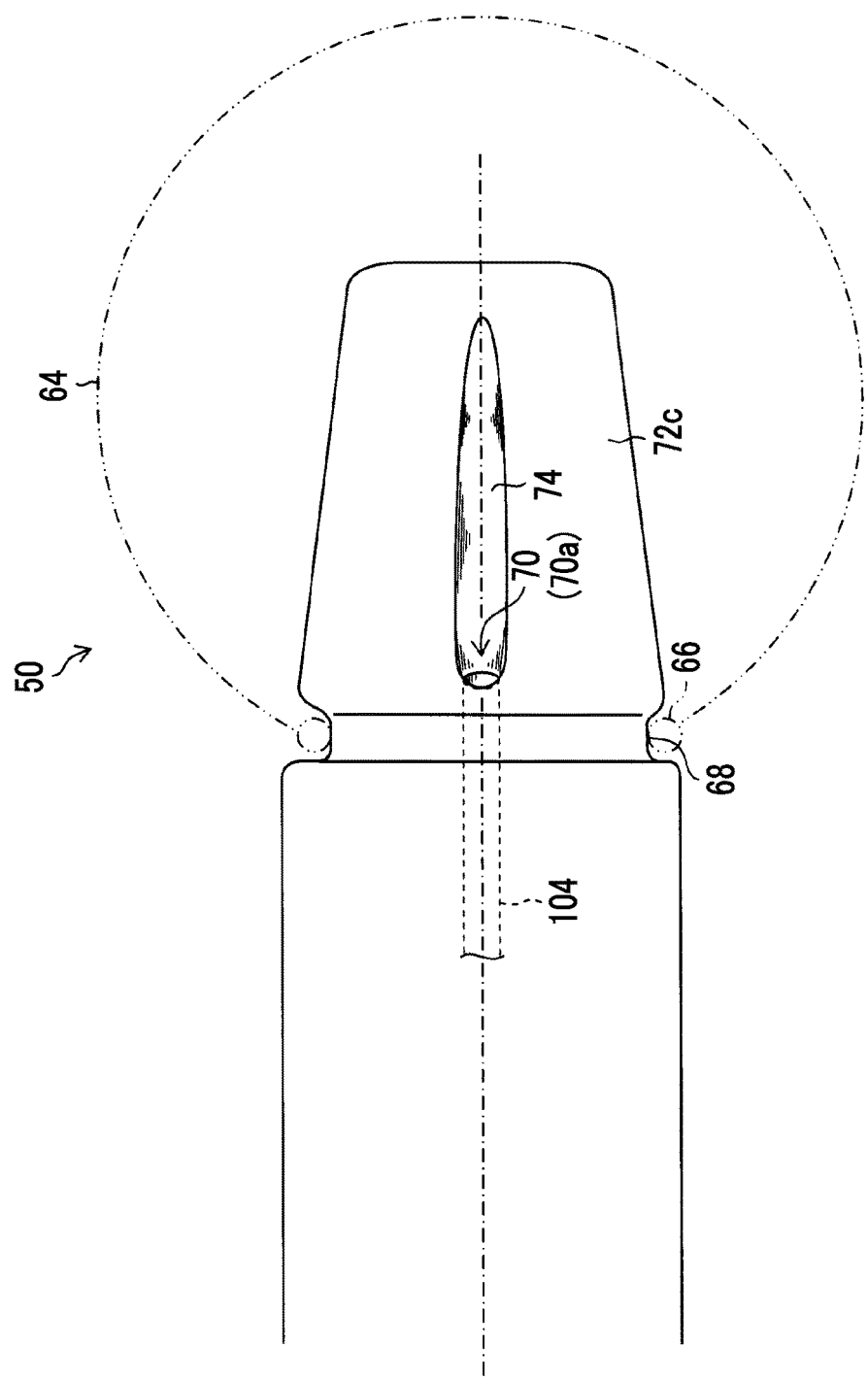
FIG. 10 is a view showing a structure in which a groove portion is formed on a bottom wall portion of the housing member.

Moreover, the structure in which the groove portion 74 is provided at the left side wall portion 72a of the pair of side wall portions 72a and 72b, which face each other with the ultrasonic transducer 62 interposed therebetween, of the outer wall portion of the housing member 72 when the tip portion 50 is viewed from the tip side has been described in this embodiment as shown in FIGS. 3 to 5. However, the groove portion 74 may be provided at another outer wall portion that is arranged to be parallel to the ultrasonic transducer 62. For example, as shown in FIG. 9, the groove portion 74 may be provided at the right side wall portion 72b when the tip portion 50 is viewed from the tip side. Further, as shown in FIG. 10, the groove portion 74 may be provided at a bottom wall portion 72c from which the left and right side wall portions 72a and 72b are erected.

According to the structure that comprises the groove portion 74 (having a notched shape) formed by notching a part of the outer wall of the housing member arranged to be parallel to the ultrasonic transducer 62 in this way, it is possible to reduce the size and diameter of the tip portion 50 without increasing the outer diameter of the tip portion 50. Particularly, since the groove portion 74 is formed so that at least a part of the groove portion 74 overlaps the ultrasonic transducer 62 in the direction of the longitudinal axis of the insertion part 20, it is possible to significantly reduce the size of the tip portion 50 in the direction of the longitudinal axis of the insertion part 20 in comparison with a structure in which the groove portion 74 does not overlap the ultrasonic transducer 62.

As shown in FIGS. 3 to 5, the housing member 72 where the groove portion 74 and the supply/discharge port 70a are formed does not need to be formed of a single member and may be formed of a plurality of members. For example, the housing member 72 may include a tip-side housing member that holds the ultrasonic transducer 62 and a base end-side housing member that is connected to the locking groove 68, and a base end side of the groove portion 74 and the supply/discharge port 70a may be formed at the base end-side housing member.

The ultrasonic endoscope according to the invention has been described in detail above, but the invention is not limited to the above-mentioned embodiment. It goes without saying that the invention may have various improvements and modifications without departing from the scope of the invention.

EXPLANATION OF REFERENCES

10: ultrasonic endoscope
12: ultrasonic processor device
14: endoscopic processor device
16: light source device
18: monitor
20: insertion part
22: operation unit
24: universal cord
50: tip portion
52: bendable portion
54: soft portion
44: treatment tool insertion opening
60: ultrasonic observation unit
62: ultrasonic transducer
64: balloon
68: locking groove
70: tip-side opening surface
70a: supply/discharge port
72: housing member
74: groove portion
80: endoscopic observation unit
82: observation portion
84: illumination portion
86: inclined surface portion
88: observation window
92: air supply/water supply nozzle
94: treatment tool outlet
96: elevator
104: balloon pipe line

What is claimed is:

1. An ultrasonic endoscope comprising:
an insertion part that includes a tip, a base end, and a longitudinal axis;
an ultrasonic transducer that is provided at the tip of the insertion part;
a balloon mounting portion which is disposed closer to the base end of the insertion part than the ultrasonic transducer is and on which a balloon wrapping the ultrasonic transducer is detachably mounted;
a supply/discharge pipe line for a balloon that extends in the insertion part;
a groove portion which is formed along the longitudinal axis and includes a base end surface that is provided closer to the tip than the balloon mounting portion in a direction of the longitudinal axis, the base end surface being provided on a surface intersecting the longitudinal axis, and a side surface that is extended from the base end surface toward a distal direction along the longitudinal axis, wherein at least a part of a range in the direction of the longitudinal axis overlaps a range of the ultrasonic transducer in the direction of the longitudinal axis; and
a tip-side opening surface of the supply/discharge pipe line for a balloon, the tip-side opening surface being provided on the base end surface of the groove portion and having components normal to a direction of the longitudinal axis.

2. The ultrasonic endoscope according to claim 1, wherein the groove portion includes a straight groove that extends from the tip-side opening surface in the direction of the longitudinal axis, and an inclined groove which extends from the straight groove so as to be inclined with respect to the direction of the longitudinal axis and of which a depth is gradually reduced toward the tip.

3. The ultrasonic endoscope according to claim 1, wherein a base end side of the groove portion extends toward the base end beyond the tip-side opening surface and the depth of the groove portion is reduced toward the base end.

4. The ultrasonic endoscope according to claim 1, wherein the groove portion is provided at any one of a pair of side wall portions that face each other with the ultrasonic transducer interposed therebetween.

5. The ultrasonic endoscope according to claim 1, wherein the groove portion is provided at a bottom wall portion from which a pair of side wall portions facing each other with the ultrasonic transducer interposed therebetween are erected.

6. The ultrasonic endoscope according to claim 1, wherein the groove portion extends up to a position that is closer to the base end than a tip surface of the insertion part.

7. The ultrasonic endoscope according to claim 1, wherein the groove portion extends up to a tip surface of the insertion part.

* * * * *